US00PP09952P

United States Patent [19]

Fruehwirth

[11] Patent Number: Plant 9,952

[45] Date of Patent: Jul. 8, 1997

[54] POINSETTIA PLANT NAMED '603'

[75] Inventor: Franz Fruehwirth, Encinitas, Calif.

[73] Assignee: Paul Ecke Ranch, Inc., Encinitas, Calif.

[21] Appl. No.: 621,003

[22] Filed: Mar. 22, 1996

[51] Int. Cl.[6] ..... A01H 5/00

[52] U.S. Cl. ..... Plt./86.4

[58] Field of Search ..... Plt./86.4

*Primary Examiner*—Howard J. Locker

*Attorney, Agent, or Firm*—Arnold, White & Durkee

[57] ABSTRACT

Poinsettia '603' is a new cultivar, distinguished by dark red flower bracts, dark green foliage, self-branching characteristics, compact upright growth habit and 8-week flowering response time. The new plant produces a very desirable branched flowering pot plant for early to mid-season holiday market. Poinsettia '603' is resistant to epinasty after being confined to shipping containers. The post-production foliage and bract retention are excellent even under low light intensities in the consumer's home.

2 Drawing Sheets

BACKGROUND OF THE NEW PLANT

The new poinsettia cultivar, '603', originated as an induced self-branching sport of a seedling known as 'H-62' (not patented) in my greenhouse in Encinitas, Calif. It was selected because of its dark, rich red flower bracts, dark green foliage, self branching characteristics, and upright growth habit; traits that distinguish it from other poinsettia cultivars, and seem to make it a desirable plant for commercial greenhouse production. After selection, '603' was vegetatively reproduced from stem cuttings for test purposes in Encinitas, Calif. 'H-62' is a proprietary plant and there are no specimens in the public domain. Poinsettia 'H-62' is not self-branching in that no axillary branches develop as long as the apical bud is not removed (pinched). '603' is self-branching in that during development axillary branches elongate without removal of the apical bud. Under short day conditions, the axillary branches will develop flowers.

Poinsettia '603' most closely resembles poinsettia '409' (U.S. Plant Pat. No. 7,825), but differs in these aspects: '603' has a more compact and upright growth habit and fewer cyathia than '490' under the same cultural conditions. By subjecting clones of this plant to successive generations of vegetative propagation, it was demonstrated that the distinctive characteristics of '603' held true from generation to generation.

DESCRIPTION OF THE PHOTOGRAPHS

Poinsettia '603' is illustrated in the accompanying color photographs.

DESCRIPTION OF THE PLANT

Figure 1:
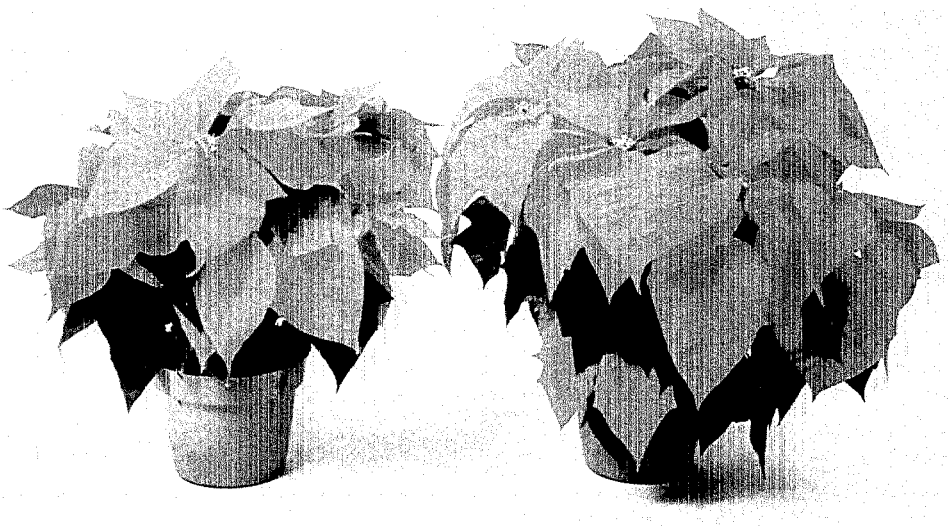
FIG. 1 is a side view of a branched '603' plant, left, compared to another dark leafed cultivar '490', right, in full flower.
Figure 2:
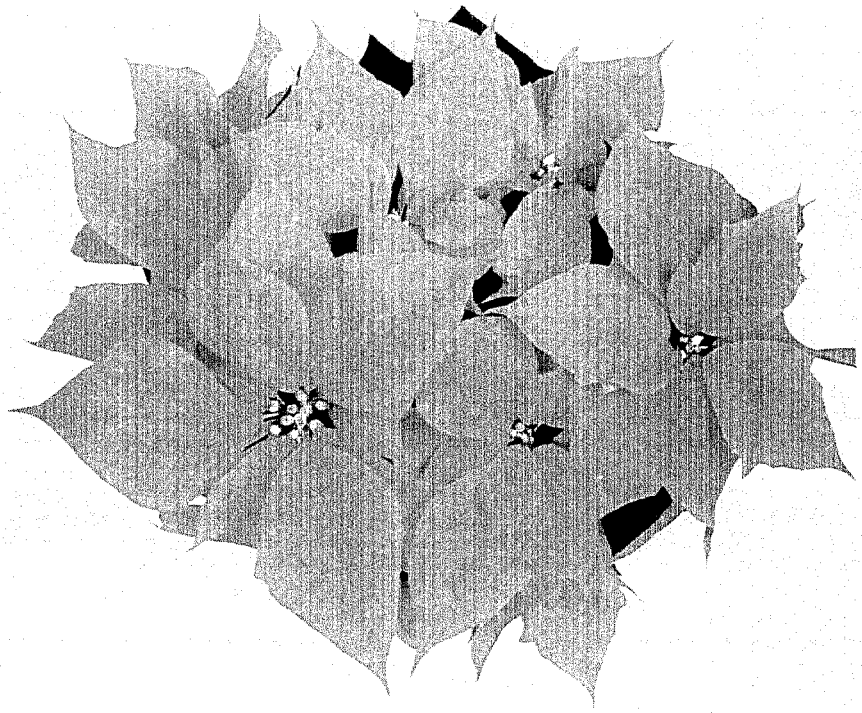
FIG. 2 is a top view of the same '603' plant showing flower and bract formation.

The following is a detailed description of this new poinsettia as observed in Encinitas, Calif. USA during Dec. 1994. Observations were recorded from flowering plants, grown as one branched plant per pot. The pot was 14 cm in diameter and 11 cm in height. Color designations are compared to the 1986 edition of R.H.S. Colour Chart, first published in 1966 by The Royal Horticultural Society, London, England.

THE PLANT

The following chart summarizes some of the differences between Poinsettia '603' and the plant it most closely resembles, Poinsettia '490' (U.S. Plant Pat. No. 7,825) under the same cultural conditions.

| Plant | '603' | '490' |
|---|---|---|
| Overall height | 38 cm | 43 cm |
| Overall width | 35 cm | 45 cm |
| Bract diameter | 24 cm | 30 cm |
| Leaf dimensions | 12 × 8 cm | 14 × 10 cm |
| No. of Bracts | 10–12 | 16–18 |
| Bract dimensions | 14 × 9 cm | 17 × 10 cm |
| Bract color | RHS 46A-B | RHS 45A |
| No. of cyathia | 4–5 | 14–15 |

Origin: Sport of a seedling. The sport was induced by application of the procedures set forth in U.S. Pat. No. 4,724,276, incorporated herein by reference, to the seedling plant. Root stock used was 'Annette Hegg Dark Red' (U.S. Plant Pat. No. 3,160).

Classification:

*Botanical.*—*Euphorbia pulcherrima* Willd.

*Common name.*—Poinsettia.

*Cultivar name.*—'603'.

Form: Shrub.

Height: Short.

Growth habit: Single stemmed plant, upright and vigorous with self-branching side shoots. The application of a chemical growth retardant may not be needed to restrict height for commercial pot plant production. I observed a branched plant in a pot with an overall height of 38 cm and an overall width of 35 cm. The bract diameter of individual flowers was 24 cm.

Branching: Axillary branches will develop and terminate in a flower without pinching. However, it is usually desirable to pinch '603' before flower induction and remove all terminal dominance. Then, all axillary branches will develop uniformly and at a faster rate.

Growth rate: Rooting of stem cutting occurs in 12–18 days under intermittent mist. The plant will flower in about eight weeks under continuous long night conditions and night temperatures of about 16–18 degrees C.

Foliage: The foliage is clean and uniformly dark green from bottom to top of the plant. The leaves are of medium size, leaf blades typically 12 cm long and 8 cm wide with leaf petioles 4 cm long and deep red. The upper leaf surface is glabrous and the under surface is finely pubescent.

*Leaf shape.*—Typical leaves are generally ovate with acute to obtuse bases and acuminate tips. Leaf margins are lobed with 1 or 2 indentations on each side of the leaf blade.

*Color.*—Upper side — Dark green, darker than R.H.S. 147A. Under side — Green, near R.H.S. 147A.

*Retention.*—The foliage lasts extremely well even under low light intensities in the consumer's home.

Bracts: Generally there are 10–12 rich red bracts of various sizes subtending the cyathia. The primary bracts have blades typically 14 cm long and 9–10 cm wide with petioles about 2 cm long.

*Shape.*—Primary bracts are ovate with acute bases and acuminate tips. Primary bract margins are entire or modestly lobed with 1 or 2 indentations on either side of the bract. Secondary bracts are of various sizes, ovate to elliptical, slightly rugose and have entire margins.

*Color.*—Upper side — Rich, dark red, between R.H.S. 46A-B. Under side — Red, R.H.S. 46B-53B.

Flowers: Generally, 4–5 cyathia (flowers) are present when the plant is in full bloom. Each cyathium is about 6 mm long and 5 mm wide, green in color, and fringed with red at the distal end. A yellow nectar cup protrudes from the side of each cyathium. The flower pedicel is also green and about 5 mm in length. The stamens protruding from the cyathia are dark red. The anthers are bifurcate; the pollen is yellow and copious. The stigmas are dark red and trifurcate.

*Nectar exudate.*—Abundant.

*Seeds.*—Self-incompatible.

*Fertility.*—Not observed.

Post production: Poinsettia '603' is resistant to epinasty after being confined to shipping containers and retains its leaves and flower bracts for several weeks in the consumer's home environment.

What is claimed is:

1. A new and distinct cultivar of Poinsettia plant, substantially as herein shown and described, distinguished by its dark red flower bracts, dark green foliage, self-branching characteristics and compact upright growth habit.

* * * * *